US012646184B2

(12) United States Patent
Lai et al.

(10) Patent No.: US 12,646,184 B2
(45) Date of Patent: Jun. 2, 2026

(54) SYSTEM AND METHOD FOR TISSUE ANALYSIS USING REMOTE PPG

(71) Applicant: KONINKLIJKE PHILIPS N.V., Eindhoven (NL)

(72) Inventors: Marco Lai, Eindhoven (NL); Bernardus Hendrikus Wilhelmus Hendriks, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/839,007

(22) PCT Filed: Feb. 15, 2023

(86) PCT No.: PCT/EP2023/053778
§ 371 (c)(1),
(2) Date: Aug. 15, 2024

(87) PCT Pub. No.: WO2023/156472
PCT Pub. Date: Aug. 24, 2023

(65) Prior Publication Data
US 2025/0166209 A1      May 22, 2025

(30) Foreign Application Priority Data

| Feb. 18, 2022 | (EP) | ..................................... 22157397 |
| Feb. 18, 2022 | (EP) | ..................................... 22157440 |
| Jan. 29, 2023 | (WO) | ................. PCT/EP2023/052103 |

(51) Int. Cl.
*A61B 5/026* (2006.01)
*A61B 1/05* (2006.01)
(Continued)

(52) U.S. Cl.
CPC ............ *G06T 7/246* (2017.01); *A61B 5/0261* (2013.01); *G06T 7/0012* (2013.01); *G06T 7/30* (2017.01);
(Continued)

(58) Field of Classification Search
CPC ............................ G06T 7/0012; G06T 7/0014
See application file for complete search history.

(56) References Cited

U.S. PATENT DOCUMENTS

| 2015/0164592 A1* | 6/2015 | Elhawary ............. A61B 5/0084 |
| | | 600/479 |
| 2017/0079530 A1 | 3/2017 | Dimaio |
(Continued)

FOREIGN PATENT DOCUMENTS

| CN | 111297343 A | 6/2020 |
| CN | 111329463 A | 6/2020 |
(Continued)

OTHER PUBLICATIONS

Van Gastel, Mark, Sander Stuijk, and Gerard de Haan. "Motion robust remote-PPG in infrared." IEEE Transactions on Biomedical Engineering 62.5 (2015): 1425-1433.*
(Continued)

*Primary Examiner* — Carolyn A Pehlke

(57) ABSTRACT

A PPG imaging system and method is provided for processing 3D images to derive remote PPG signals. A surface mesh of a region of interest is created from each of a set of the 3D images. The surface meshes are matched to each other using mesh transformations thereby providing motion compensation. A remote PPG signal is then obtained from each of a set of mesh locations of the matched surface meshes, thereby to derive a set of PPG signals. A perfusion map and/or a PPG delay map may be obtained from the set of PPG signals.

16 Claims, 8 Drawing Sheets

(51) Int. Cl.

| | | |
|---|---|---|
| *G06T 7/00* | (2017.01) | |
| *G06T 7/246* | (2017.01) | |
| *G06T 7/30* | (2017.01) | |

(52) U.S. Cl.
CPC ....... *A61B 1/05* (2013.01); *G06T 2207/10021* (2013.01); *G06T 2207/10024* (2013.01); *G06T 2207/10028* (2013.01); *G06T 2207/10068* (2013.01); *G06T 2207/30028* (2013.01); *G06T 2207/30076* (2013.01); *G06T 2207/30104* (2013.01)

(56) References Cited

U.S. PATENT DOCUMENTS

| | | | | |
|---|---|---|---|---|
| 2020/0359884 | A1* | 11/2020 | Swisher | ............... A61B 1/3137 |
| 2021/0259567 | A1 | 8/2021 | Dellimore | |
| 2021/0369355 | A1 | 12/2021 | Masaki | |
| 2021/0401298 | A1* | 12/2021 | Levi | ..................... A61B 5/7225 |
| 2022/0354418 | A1 | 11/2022 | Bourquin | |
| 2024/0041342 | A1 | 2/2024 | Lai | |

FOREIGN PATENT DOCUMENTS

| | | | | |
|---|---|---|---|---|
| CN | 112270693 | A | 1/2021 | |
| WO | 2010082748 | A2 | 7/2010 | |
| WO | 2019045971 | A1 | 3/2019 | |
| WO | WO-2021074097 | A1 | * | 4/2021 | ........... A61B 5/0077 |

OTHER PUBLICATIONS

Prescient.com (What is Mesh and what are the types of Meshing; www.pre-scient.com/knowledge-center/product-development-by-reverse-engineering/mesh/; Feb. 19, 2019).*

International Search Report and Written Opinion of PCT/EP2023/053778, dated May 22, 2023.

Nagamatsu, Genki et al "PPG3D: Does 3D Head Tracking Improve Camera-Based PPG Estimation?", 42nd Annual International Conference of the IEEE Engineering in Medicine & Biology Society, Jul. 2020, pp. 1194-1197.

Lai, Marco et al "Perfusion Monitoring by Contactless Photoplethysmography Imaging", IEEE 16th International Symposium on Biomedical Imaging, Apr. 2019.

Besl, P.J. et al "A Method for Registration of 3-D Shapes", IEEE Transcations on Pattern Analysis and Machine Intelligence, IEEE Computer Society, vol. 14, No. 1, Feb. 1992, pp. 239-256.

Zhang, Chen et al "Real-Time Multimodal 3D Imaging System for Remote Estimation of Vital Signs", Proceedings of the SPIE, vol. 11785, Jun. 2021.

Lai, Marco, PR-TN 2016/00448, "Perfusion monitoring by non-contact photoplethysmographic (PPG) imaging", 2017.

Lai, Marco et al "Evaluation of a Non-contact Photo-Plethysmographic Imaging (iPPG) System for Peripheral Arterial Disease Assessment", SPIE Medical Imaging, 2021.

Lucas, Bruce D. et al, "An Iterative Image Registration Technique with an Application to Stereo Vision", Proceedings of Imaging Understanding Workshop, pp. 121-130, 1981.

Fouladi, Seyyed Hamed et al "Extracting Remote Photoplethysmogram Signal from Endoscopy Videos for Vessel and Capillary Density Recongition", 38th Annual International Conference of the IEEE Engineering in Medicine and Biology Society, Aug. 2016, pp. 227-230.

Schneider, David C. et al "Deshaking Endoscopic Video for Kymography", Conference Paper,. Aug. 2011.

Papazov, C. et al "Deformable 3D Shape Registration Based on Local Similarity Transforms" Computer Graphics Forum, vol. 30, No. 5, pp. 1493-1502, 2011.

Raviv, D. et al "Volumetric Heat Kernel Signatures", Proceedings of the ACM Workshop on 3D Object Retrieval, pp. 39-44, Oct. 2010.

Ikemoto, L. et al "A Hierarchical Method for Aligning Warped Meshes", Fourth International Conference on 3-D Digital Imaging and Modeling, pp. 434-441, 2003.

Chang, W. et al "Automatic Registration for Articulated Shapes", Computer Graphics Forum, vol. 27, No. 5, pp. 1459-1468, 2008.

* cited by examiner a)

b)

Time(s)

SYSTEM AND METHOD FOR TISSUE ANALYSIS USING REMOTE PPG

CROSS-REFERENCE TO PRIOR APPLICATIONS

This application is the U.S. National Phase application under 35 U.S.C. § 371 of International Application No. PCT/EP2023/053778, filed on Feb. 15, 2023, which claims the benefit of European Patent Application No. 22157397.5, filed on Feb. 18, 2022 and European Patent Application No. 22157440.3, filed on Feb. 18, 2022 and International Application No. PCT/EP2023/052103, filed on Jan. 29, 2023. These applications are hereby incorporated by reference herein.

FIELD OF THE INVENTION

This invention relates to the analysis of tissue using photoplethysmography (PPG) analysis. The invention provides for a processors, systems including such processors, methods and computer programs for implementing the methods on e.g. such processors or systems.

BACKGROUND OF THE INVENTION

Microcirculation is the circulation of the blood in the smallest blood vessels, present in the vasculature embedded within organ tissues. The structure of the microvasculature is extremely complex, as so many capillaries are present in the tissues, with the individual capillaries so convoluted that the blood flow at any given point in any given capillary could be in any direction. For this reason, it can be stated that their overall function becomes averaged. That is, there is an average rate of blood flow through each tissue capillary bed, an average capillary pressure within the capillaries, and an average rate of transfer of substances between the blood of the capillaries and the surrounding interstitial fluid. This is the perfusion of the tissue.

Organ perfusion is a crucial indicator of injury and disease, which may include inflammation, stagnant or stopped blood flow, and all pathologies that can lead to global tissue hypoxia and organ dysfunction. Perfusion monitoring can be used to assess these microvascular injuries and many others, such as the progress of healing of either burned skin or wounds or the recovery of the perfusion downstream of a vessel lesion, and the necrosis (e.g., foot ulceration, sepsis) for patients with diabetes.

Non-contact PPG imaging is a recent emerging technology able of monitoring skin perfusion. PPG imaging utilizes an off-the-shelf camera and a light source to remotely detect the dynamic changes in blood volume beneath the skin and allows extracting blood pulsation signals. PPG imaging allows for the elaboration of large tissue areas, thus building a so-called perfusion map, which is a great advantage with respect to contact PPG. PPG imaging has shown to be capable of detecting skin perfusion perturbations, such as irritation, temperature changes and even flow blockage during pressure measurements and has even been evaluated for peripheral arterial disease assessment.

It is possible to build an amplitude map, that represents the amplitude of the PPG signal per image sensing pixel. Furthermore, it is also possible to build a delay map, which provides a measure of the average time delay between the PPG signal wave of each pixel and a reference PPG signal. There is a small delay in the blood pulsation arrival, due to small differences in the microcirculatory bed, such as the resistance and elasticity of the vessels, as well as different artery branches that supply the recorded tissues.

For the purposes of this application, which relates to processing of non-contact PPG signals, perfusion may be defined as the amplitude of a PPG signal of the tissue, namely the amplitude of the pulsatility extracted from the tissue.

To extract a reliable PPG signal and perfusion map, it is important that each pixel of the image looks at the same small region of the skin. Thus, instead of looking at a video as a series of frames acquired by the camera one after the other, the video images can be considered as a matrix of light sensors that detect the variation in light in small regions of the skin, stored in the pixels of the video.

Motion stabilization is needed for compensating for motion. Usually stabilization is needed when a camera is not still, for example if an operator is holding it or if a video is recorded on a not stable support. Also, it is not possible for the subject to stay completely still during the measurements, some motions will be always present and as a result the sensors of the camera will not always look at the same small regions of investigation.

This issue can be solved by implementing a correction via motion stabilization software. Once video is acquired, the motion stabilization algorithm will stabilize the region of investigation so that in a given pixel there will always be the signal of the same small region of skin.

SUMMARY OF THE INVENTION

Unfortunately, in some situations, such as when endoscopic images are acquired inside the body, motion stabilization on the image becomes extremely difficult. Organs and internal body areas in general undergo deformation, and operators cannot hold the endoscope in a fixed situation for long, causing perspective changes. Because of these factors, motion compensation is very hard in these situations.

There is therefore a need for improved motion compensation when collecting remote PPG signals.

The invention is defined by the claims.

According to examples in accordance with an aspect of the current disclosure, there is provided a processor for a PPG imaging system and a PPG imaging system, each for processing 3D images to derive remote PPG signals, the processor being adapted to:

receive 3D images of a region of interest;

construct a surface representation of the region of interest from each of a set of the 3D images;

match the surface representations to each other using transformations thereby providing motion compensation; and derive a remote PPG signal from each of a set of locations of the matched surface representations, thereby to derive a set of PPG signals.

This system makes use of remote PPG sensing to derive a set of PPG signals, for example a PPG perfusion map and/or a PPG delay map.

The remote PPG signals are obtained by analyzing image changes, for example changes in color over time, at specific locations of the region of interest. The images thus need to be aligned with each other to be able to track the images at specific locations. This alignment is particularly difficult in some situations, for example when the images are obtained using an endoscope or other medical system that is used to image regions with high motility during imaging such as those of organs of a living subject. Motion compensation is needed to compensate for the relative movement between the imaging camera and the region of interest. This can be caused by movement of the camera, movement of the region of interest or both.

The motion compensation is achieved by creating a 3D surface (e.g. mesh, pointcloud, or other) representation of each image of the target area (including the region of interest), and using this surface representation to align multiple meshes, pointclouds or other surface representations acquired at consecutive moments in time. The transformations of surface representations is used to make them mutually match. In this way, PPG signals can be extracted from each location, after the surface representations have been aligned. In this way PPG signals are extracted that pertain to a surface representation location instead of an image location (pixel location) which makes the signals less- or even in-dependent on relative motion of the region of interest with respect to an image camera. The derived set of PPG signals thus pertain to a representation of a region of interest. The set of PPG signals for example comprise a PPG perfusion map based on PPG amplitude levels obtained from the images at the surface representation (e.g. mesh, pointcloud or otherwise spatially defined) locations.

The set of PPG signals may further comprise a PPG delay map based on PPG relative delays between different locations of the surface representation (e.g. mesh, pointcloud or other).

The obtained PPG maps can also be 3D PPG maps of perfusion, which express the amplitude of the PPG signal (or the delay of the PPG signal) in each location of the surface representation (e.g. mesh, pointcloud or other).

The delay information enables different tissue types to be identified, either automatically or by user-selection after displaying a suitable representation of the PPG delay map. Different tissue regions for example have different delay times. This may arise because the different tissue types are supplied by different arteries and hence have a different path and hence path length to the heart. This may arise in the case of different portions of the intestines, and these portions may become adjacent during open bowel resection. There is a resulting intestinal anastomosis with communication between formerly distant portions of the intestine. Hence the systems, methods defined herein are advantageous for medical imaging systems and methods such as endoscope systems and methods.

It is then of interest to analyze the perfusion in these portions separately as this gives a more accurate tissue assessment, as it takes account of the different tissue types and their possible different blood supplies.

In one example, the 3D images comprise stereo RGB camera images. In another example, the 3D images comprise depth camera images. In all cases, the 3D images may comprise endoscope images. Stereo camera images are preferred as these have improved depth information for deriving the surface representations when compared to the depth camera images.

Motion compensation in endoscope images is particularly challenging, due to the motion of the endoscope as well as motion and deformation of the tissue being imaged.

The locations may comprise or be mesh locations. In such case they may comprise vertices or faces of the matched surface meshes.

The transformations may comprise:
rigid transformations; and/or
transformations with deformation.

Thus, various different transformations may be used to match the surface representations such as the meshes, pointclouds or other representations. Transformations with deformations are preferred as they may account for highly movable deformable regions or interest such as internal organs of a subject during surgery. Exemplifying such organs comprise the intestine and heart.

The system for example further comprises a 3D camera for capturing the 3D images of the region of interest. The system may further comprise an endoscope, wherein the 3D camera is mounted at a distal end of the endoscope.

The current disclosure also provides a computer-implemented method for processing 3D images to derive remote PPG signals, comprising:
receiving 3D images of a region of interest;
constructing a surface representation of the region of interest from each of a set of the 3D images;
matching the surface representations to each other using transformations thereby providing motion compensation and/or shape deformation compensation; and
deriving a remote PPG signal from each of a set of locations of the matched surface representations, thereby to derive a set of PPG signals.

The method may comprise providing the set of PPG signals as a PPG perfusion map based on PPG amplitude levels obtained from the images at the mesh locations. The method may further comprise providing the set of PPG signals as a PPG delay map based on PPG relative delays between different locations such as mesh locations. 3D PPG maps may be provided of amplitude and/or delay.

Anu features described hereinbefore for processor or system may be used to define a corresponding method.

The current disclosure also provides a computer program comprising computer program code means which is adapted, when said program is run on a computer, to implement the method defined above. The computer program may be stored on a computer readable medium such as a non-transient medium. Such medium or media may include memories such as for example described hereinafter. The computer program may be downloadable from a telecommunications network such as 3G, 4G or 5G Network or from an information network such as WAN or LAN network, as known in the art. The computer may be or may comprise the processor as defined herein. The computer may be part of the PPG imaging system. The current disclosure also provides a processor which is programed with the computer program. The processor is for use in the PPG imaging system. The PPG imaging system my be part of a medical imaging system. Such imaging systems may comprise an endoscope or endoscope device or system.

These and other aspects of the current disclosure will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying schematic drawings, in which.

5
6

Figure 6:
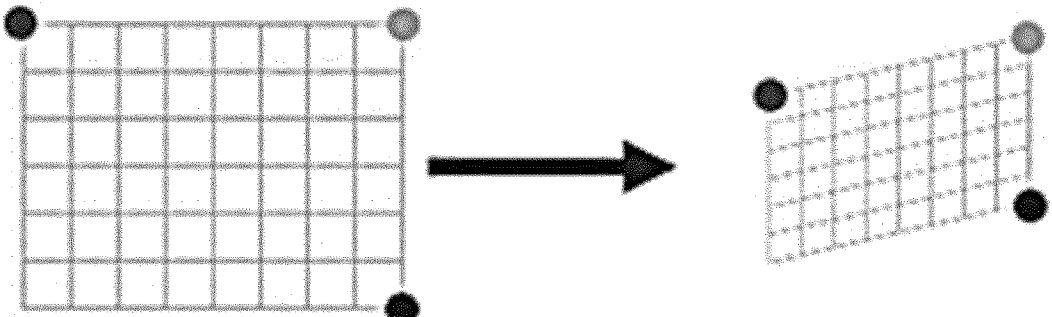
Figure 7:
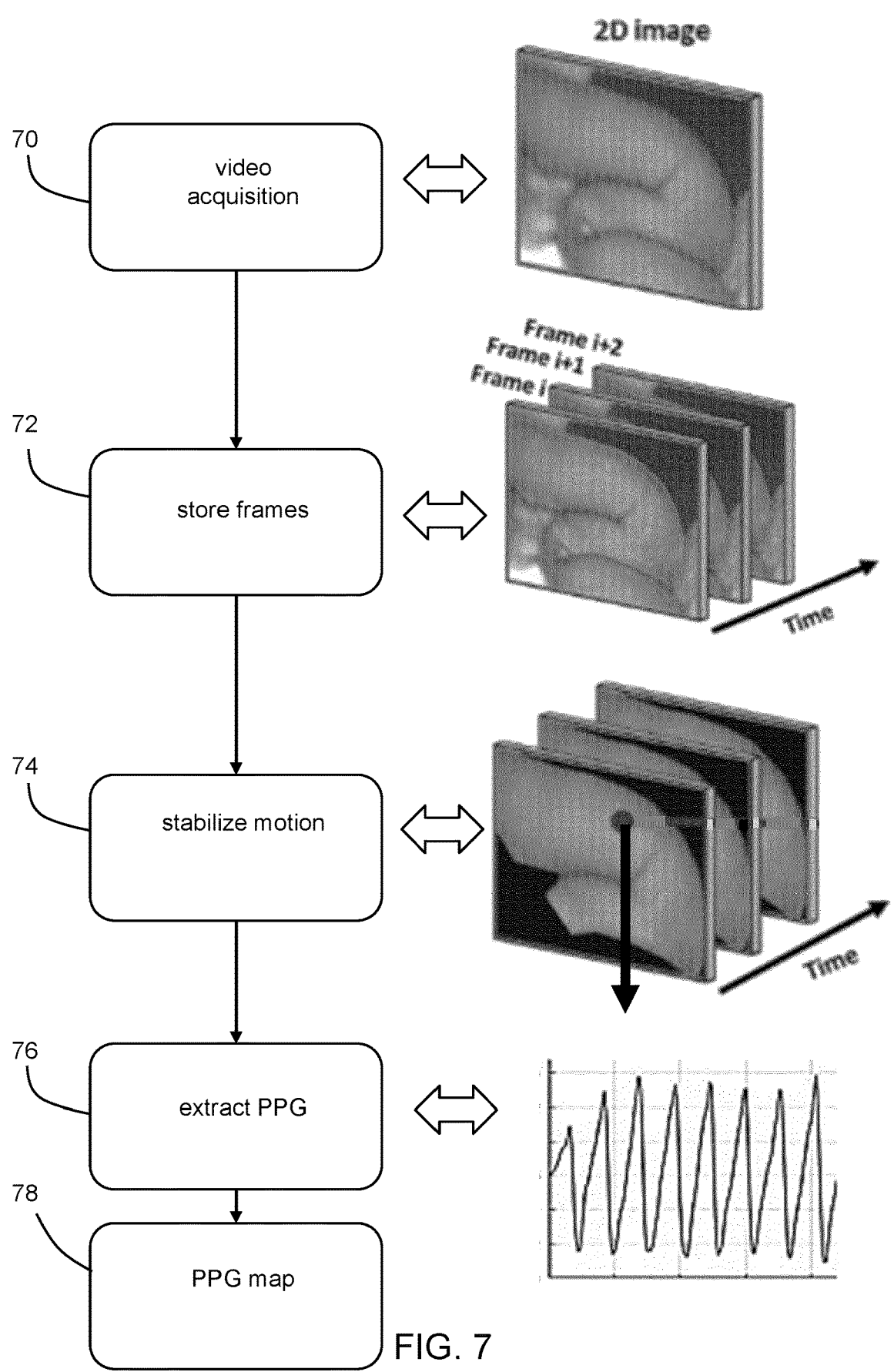
Figure 8:
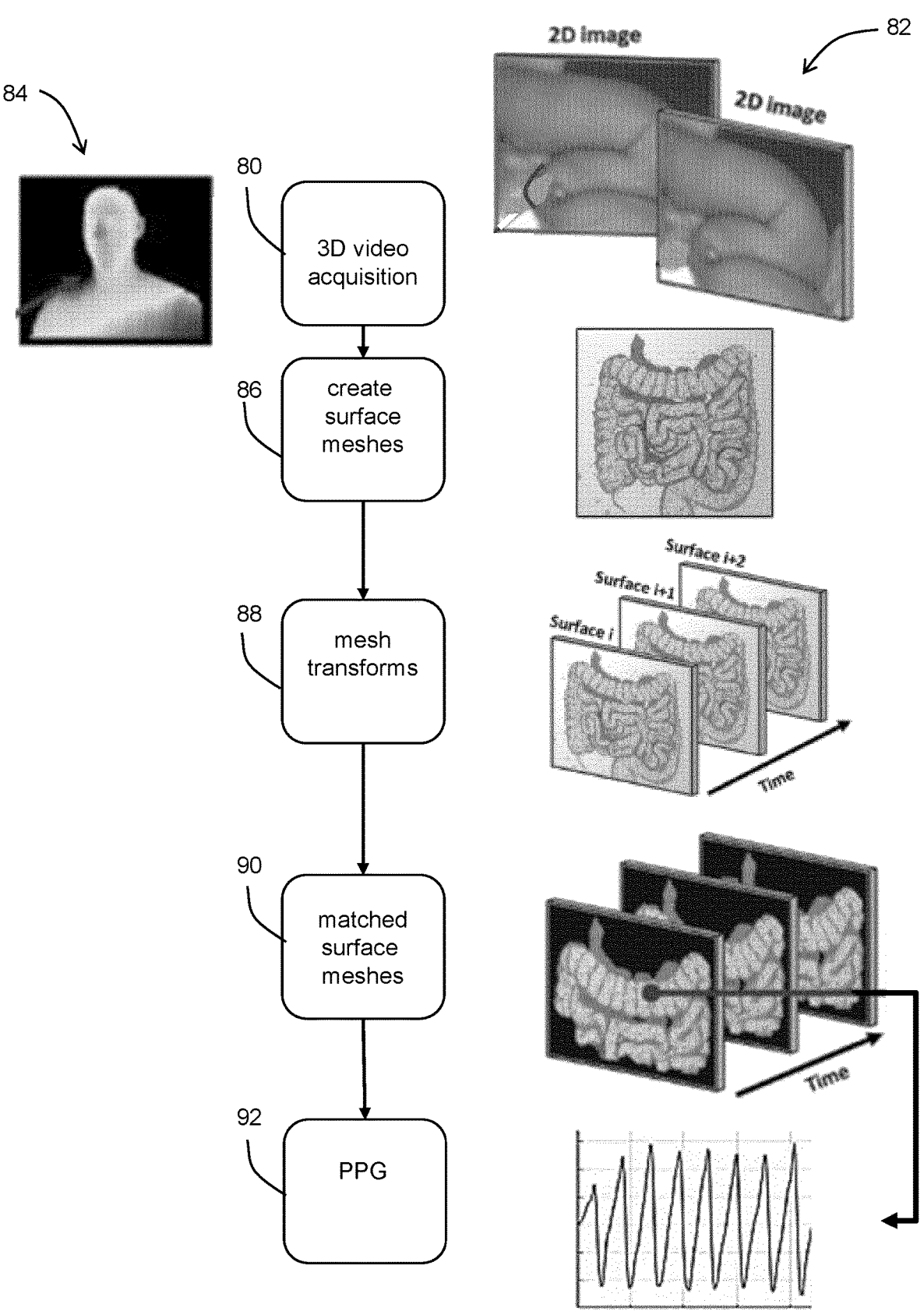
Figure 9:
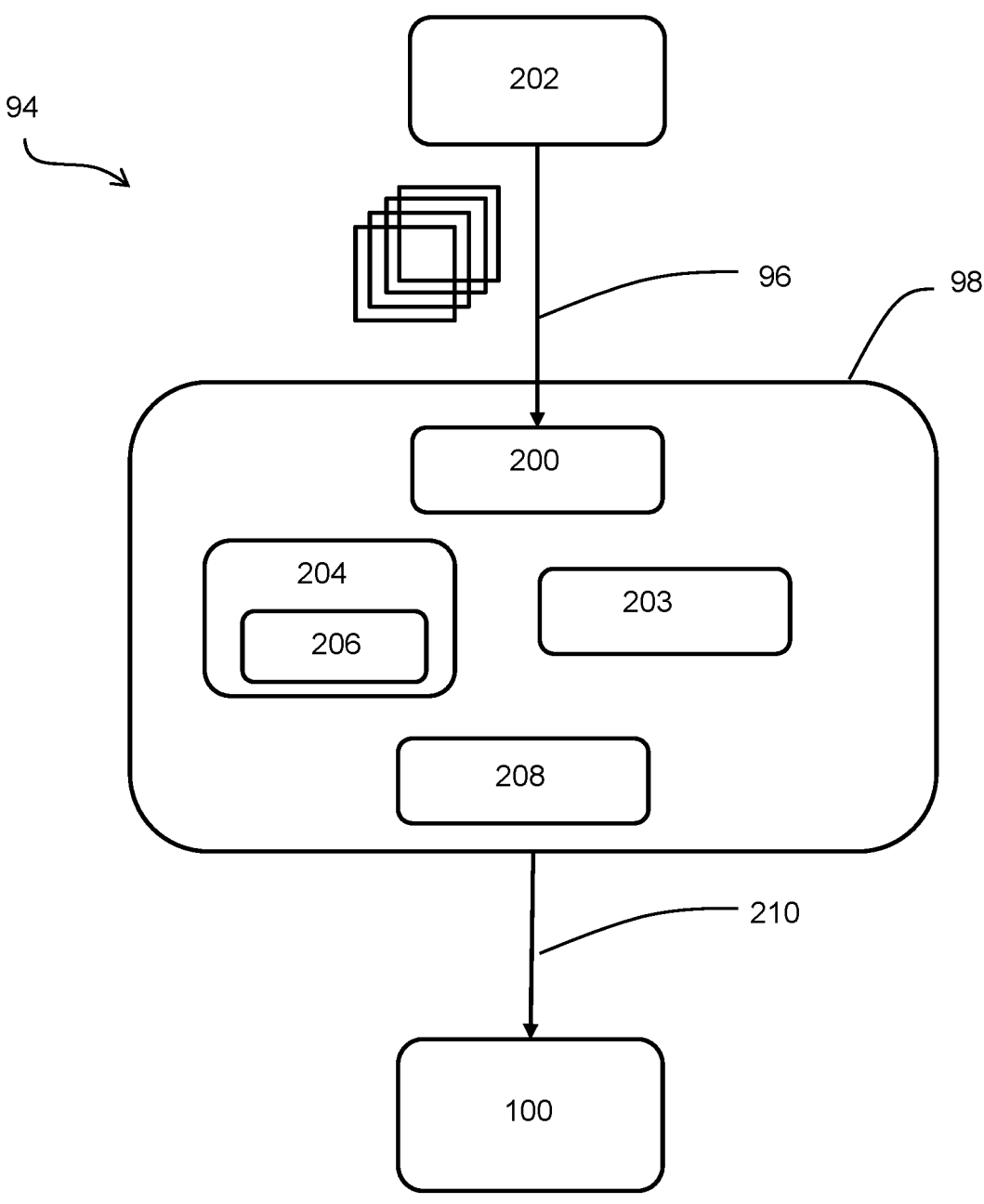
Figure 10:
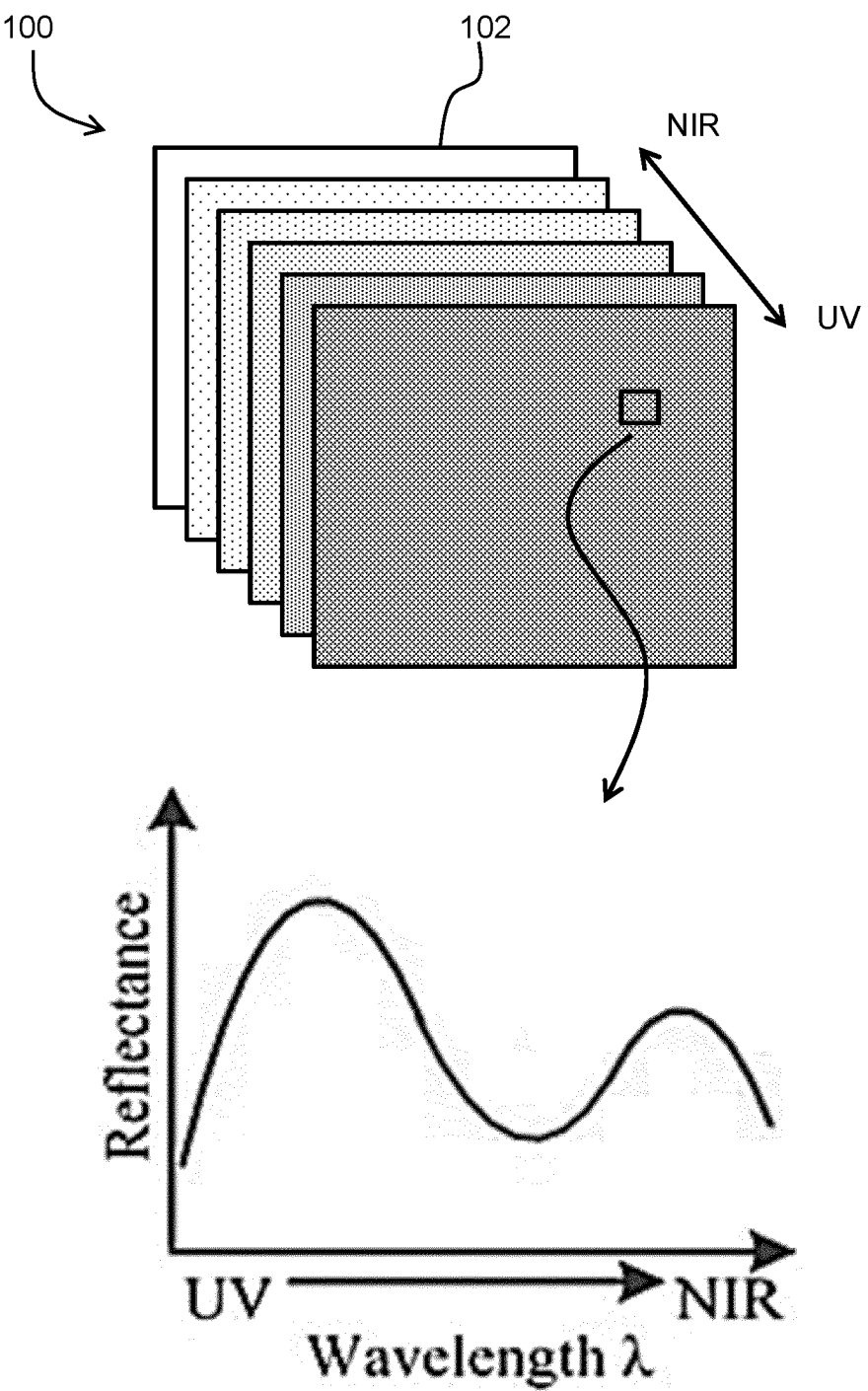

FIG. 6 illustrates an affine transformation for scaling, skewing and rotation;

FIG. 7 shows a generic approach for extracting PPG signals from pixels of a 2D endoscope and building a PPG perfusion map;

FIG. 8 shows a method for processing 3D images to derive remote PPG signals in accordance with the current disclosure;

FIG. 9 shows system as disclosed herein which may be used for tissue analysis; and FIG. 10 shows a hypercube of a hyperspectral camera;

DETAILED DESCRIPTION OF THE EMBODIMENTS

The invention will be described with reference to the Figures.

The detailed description and specific examples, while indicating exemplary embodiments of the apparatus, systems and methods, are intended for purposes of illustration only and are not intended to limit the scope of the claims. These and other features, aspects, and advantages of the apparatus, systems and methods of the present invention will become better understood from the following description, appended claims, and accompanying drawings. The Figures are merely schematic and are not drawn to scale. It should also be understood that the same reference numerals are used throughout the Figures to indicate the same or similar parts.

The current disclosure provides a PPG imaging system and method for processing 3D images to derive remote PPG signals. A surface representation, e.g. mesh or pointcloud or other, of a region of interest is created from each of a set of the 3D images. The surface representation s are matched to each other using representation transformations thereby providing motion compensation and/or shape deformation compensation. A remote PPG signal is then obtained from each of a set of locations of the matched surface representations, thereby to derive a set of PPG signals. A perfusion map and/or a PPG delay map may be obtained from the set of PPG signals, and these maps may even be 3D maps.

The examples hereinafter are described for surface representations in the form of meshes, but they will also work for other representations such as point clouds.

Before describing the system and method of the current disclosure, the known operation of a remote PPG imaging system, and the known image processing methods, will first be described.

Remote PPG imaging enables a determination of tissue perfusion from images captured of the tissue of interest, e.g. the skin or even tissue beneath the skin. Remote PPG typically uses ambient light, functioning as broad band white light source, and the diffuse and specular reflections are analyzed for different color components. Remote PPG imaging may be used to construct a PPG amplitude map and a PPG delay map.

For this purpose, a camera or a series of cameras (at one or multiple wavelengths) captures video of the tissue area, e.g. skin, at a distance. The measurements derived from the video are remote PPG images, which provide non-contact measurement of a pulse signal by analyzing subtle changes of skin color (or organ color) i.e. at different wavelengths of the light.

It has been proposed to use remote PPG for inflammation detection. It has also been proposed in European Patent Application No. 20214955.5 to measure perfusion based both on a PPG amplitude level and also information about the distribution of the PPG phases, such as a standard deviation or interquartile range of a phase map.

By extracting pulse signals at each individual location of the skin region (corresponding to each pixel of the cameras) a spatial map of the pulse signal can be derived, showing both amplitude and delay. This perfusion map thus represents the amplitude and delay of the PPG signal per pixel and hence per location of the skin.

Figure 1:
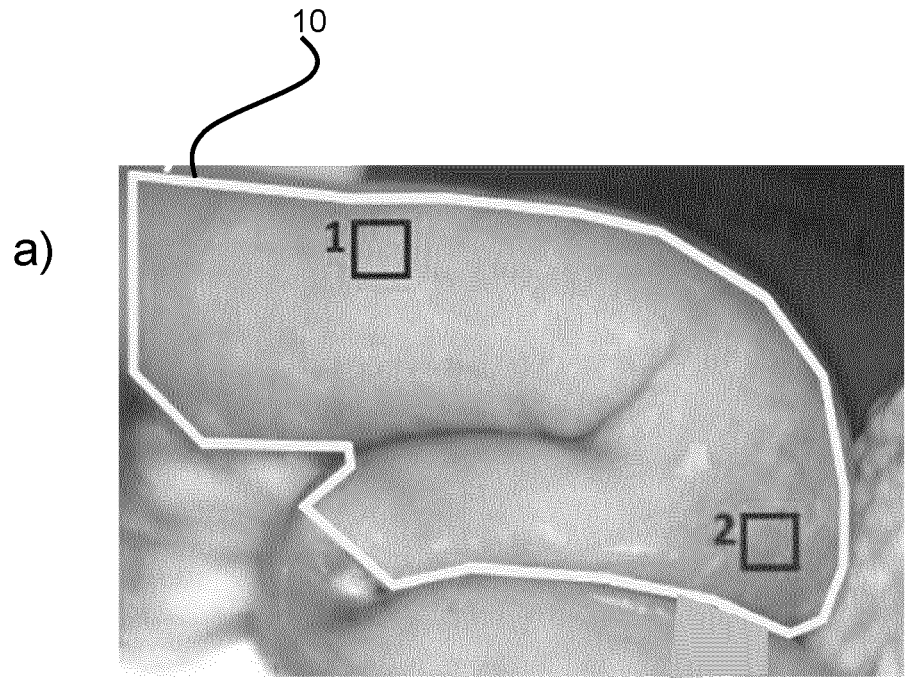
FIG. 1 shows a representation of a frame of a video acquired of the intestine and a global PPG signal derived from the video.
Figure 1:
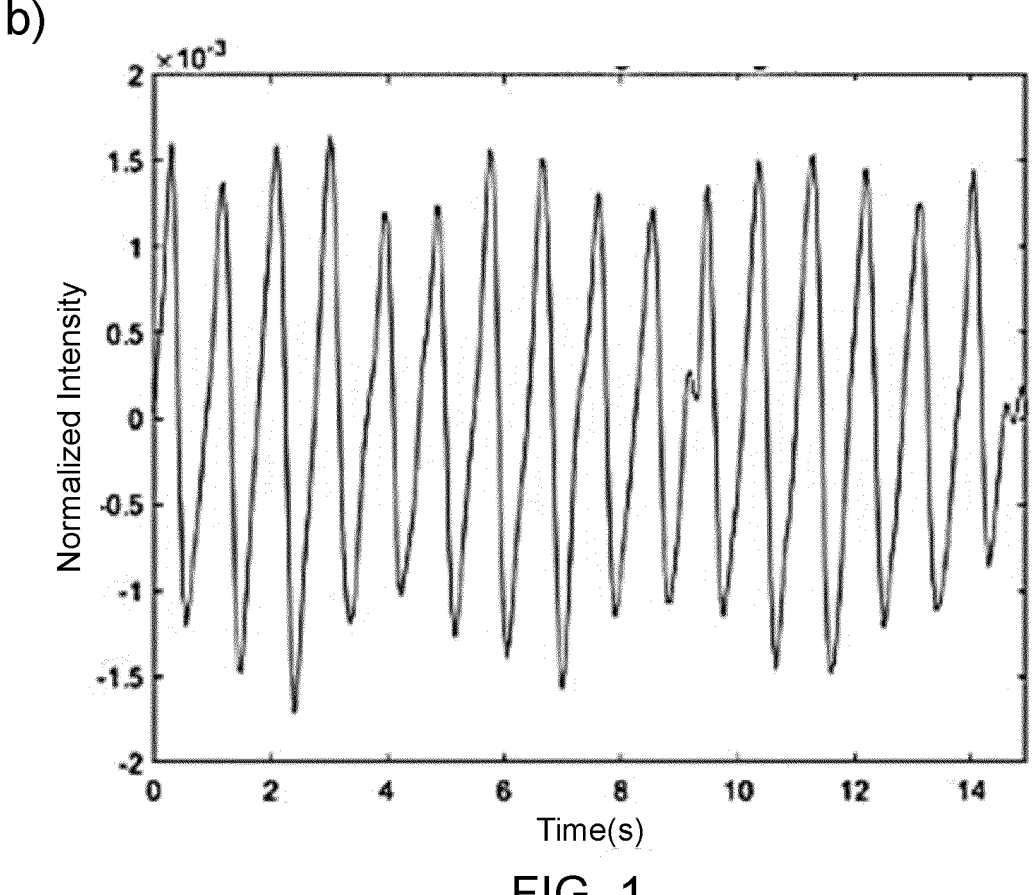

FIG. 1 (*a*) shows a representation of a frame of a video acquired of the intestine. By spatial averaging the pixel values in the region of interest (ROI) 10, a signal can be derived from the video, modulated at the heart rate. This signal is shown in FIG. 1 (*b*) as a normalized intensity of the PPG signal versus time.

The PPG signal of FIG. 1 (*b*) represents an average for the whole region of interest.

However, separate signals may also be captured from smaller regions of interest, shown as region 1 and region 2 in FIG. 1 (*a*).

Figure 2:
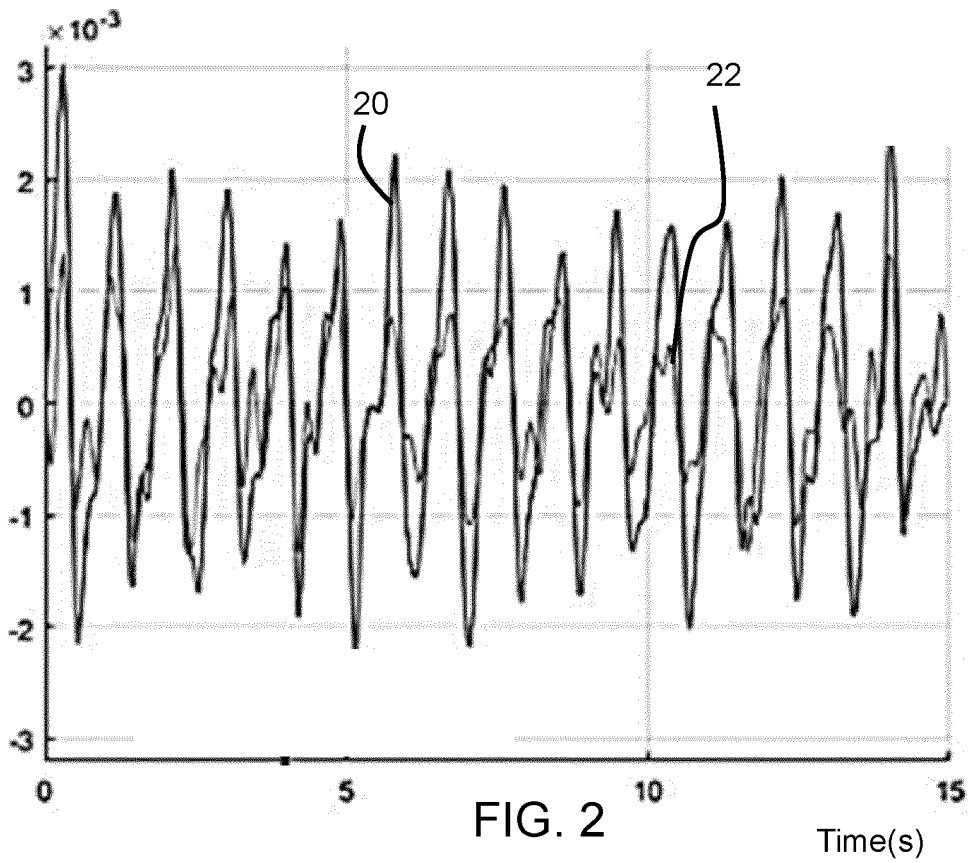
FIG. 2 shows separate PPG signals for separate regions of interest.

FIG. 2 shows separate PPG signals, as a first signal 20 for the first region of interest and a second signal 22 for the second region of interest. The two PPG signals are modulated at the same heart rate frequency, but show a different amplitude. By extracting the amplitude from the PPG signal of each separate region of tissue, i.e. from each corresponding pixel of the captured video, a PPG perfusion map may be obtained, as shown in FIG. 3.

Figure 3:
FIG. 3 shows a PPG perfusion map.

FIG. 3 is a black and white representation. However, the PPG perfusion may be color-coded, for example assigning a more red color to areas with higher perfusion and a more blue color to areas with lower perfusion. The PPG amplitude map thus represents the amplitude of the PPG signal per pixel and hence per location of the skin or other tissue being analyzed.

Additional valuable information may be obtained by analyzing the PPG signals.

Figure 4:
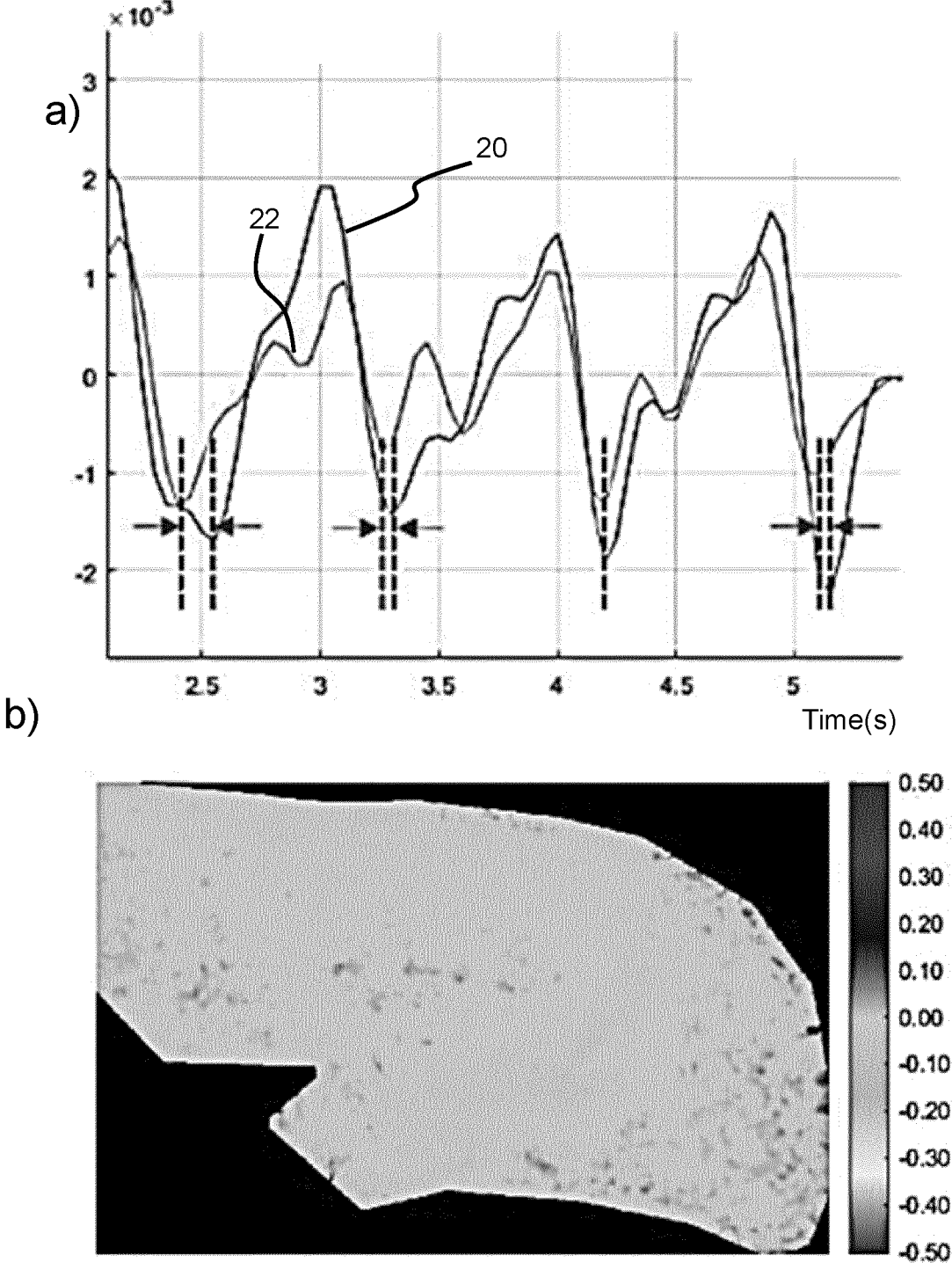
FIG. 4 shows a zoom-in of the PPG signals extracted from the two regions of interest from FIG. 2 and a PPG delay map.

FIG. 4 (*a*) shows a zoom-in of the PPG signals extracted from the two regions of interest from FIG. 2. Even though the signals are extracted simultaneously from the same organ, the pulsation arrives slightly before in one area than in the other. There is a small delay in the blood pulsation arrival, due to small differences in the microcirculatory bed, such as the resistance and elasticity of the vessels, as well as different artery branches that supply the recorded tissues.

The delays of the PPG signals of each pixel with respect to a reference signal may be extracted and used for building a delay map. The delay map is shown in FIG. 4.

Since the delay between the signals is not always constant but varies during the acquisition, an average delay is used between signals per pixel.

The average delay represents the average time delay between the PPG signal of each pixel and a reference PPG signal. In this way a signal in time is built. The length of the PPG signal should include at least a heartbeat cycle, so it is subject dependent.

The average delay is a value of delay assigned to each pixel. The plot of FIG. 4, shows a difference in time arrival between the peaks of the PPG signals. Therefore, for each pixel, the average of these delay (with respect to a reference signal) is assigned. At the end, the delay map is built, where each pixel contains the average delay between the PPG signal of that pixel and the reference PPG signal.

By acquiring a video stream, a series of images is obtained over time, for example with a frame rate of 20 frames per second. To compute the global PPG signal over time, the pixel values of the frame 1 are spatially averaged, so that the 2D set of pixels yields one value. The pixels of frame 2 are then averaged, and so on.

Eventually, a PPG signal is obtained over time (with the same length as the video that has been acquired), where each value of the signal is a spatial average of one corresponding frame of the video acquired. The image frames for example comprise 968×728 pixels, by way of example.

The PPG signal of each pixel is thus compared with the global PPG signal being used as a reference. The value assigned to each pixel "n" of the delay map thus represents the average delay between the PPG signal in the pixel "n" and the global PPG signal being used as a reference. Thus, the value of the delay for each pixel in the PPG delay map represents the average delay (in terms of average time shift) between the PPG signal of that pixel and the global PPG signal. The delays are for example computed by using the lock-in amplification algorithm.

The delay map thereby provides a measure of the average time delay between the PPG signal wave of each pixel and the reference PPG signal for at least one heartbeat cycle. The reference PPG signal is the global PPG signal of FIG. 1 (*b*) extracted from the entire region on interest of the intestine.

Since the reference signal is extracted from the entire region of interest, a PPG signal from a given location of the image is likely to be in phase with the reference.

Similar to the map of the amplitude, FIG. 4 (*b*) is a black and white representation. However, the PPG delay map may be color-coded. The Hue, Saturation, Value (HSV) color system is for example employed, since it works well with the periodicity of the PPG signal.

For extracting the amplitude maps and delay maps, a lock-in amplification method may be used.

Details on how to calculate the PPG maps using the lock-in amplification method can be found in:

(i) Lai M, Shan C, Ciuhu-Pijlman C, Izamis M L. Perfusion monitoring by contactless photoplethysmography imaging, 2019 IEEE 16th International Symposium on Biomedical Imaging (ISBI 2019) 2019 Apr. 8 (pp. 1778-1782). IEEE; and (ii) Lai M, Dicorato C S, de Wild M, Verbakel F, Shulepov S, Groen J, Notten M, Lucassen G, van Sambeek M R, Hendriks B H. Evaluation of a non-contact Photo-Plethysmographic Imaging (iPPG) system for peripheral arterial disease assessment, Medical Imaging 2021: Biomedical Applications in Molecular, Structural, and Functional Imaging 2021 Feb. 15 (Vol. 11600, p. 116000F). International Society for Optics and Photonics.

Because of the great advantages that the remote PPG technology has shown for remotely and non-invasively assessing skin-level perfusion, PPG imaging can be translated to organ perfusion assessment for detecting the perfusion of the microvasculature tissue bed beneath the organ surface, without any modification to the current acquisition setup.

The current disclosure relates to compensating for motion in the camera used to collect the images for PPG analysis and in the tissue being imaged.

Various motion stabilization algorithms are known. For example, the Kanade-Lucas-Tomasi (KLT) algorithm tracks a set of feature points across video frames so that a geometric transformation can be estimated between two frames. This algorithm allows to stabilize frames reducing motion in the region of interest, thus increasing the overlap between the same structures inside the region of interest in each frame. These transformations include rotation and translation, scaling, skewing and perspective distortion. All of them are implemented as linear transformation which are well-investigated in linear algebra.

A projective transformation is used to compensate for how perceived objects change when the view point of the observer changes. This transformation allows creating perspective distortion.

Figure 5:
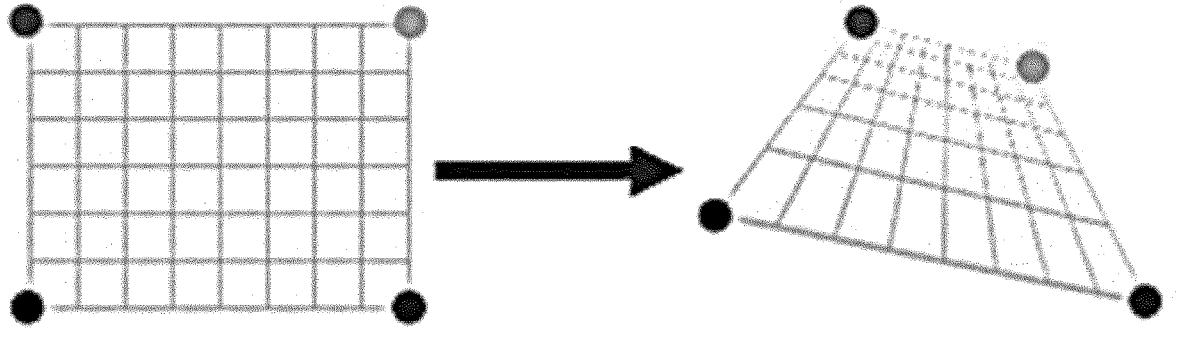
FIG. 5 illustrates a projective transformation.

FIG. 5 illustrates a projective transformation and FIG. 6 illustrates an affine transformation for scaling, skewing and rotation.

The KLT algorithm mentioned above allows features to be extracted from an image (i.e. a 2D distribution of pixels), and the extracted features are used for stabilizing a region of interest, for example using projective or affine transformations. The feature points in the KLT algorithm are corners or borders in an image, easily identifiable across different images. The features points are typically in the form of isolated points, continuous curves or connected regions.

Unfortunately, in some situations such us when endoscopic images are acquired inside the body, motion stabilization on the image is not possible. Organs and internal body areas in general undergo deformation and operators cannot hold the endoscope in a fixed situation for long, causing perspective changes. Because of these factors, motion compensation is very hard in these situations.

3D endoscopes are now becoming popular for minimally-invasive applications. These endoscopes are able to provide depth perception. They provide the surgeon with the critical ability to accurately visualize and appreciate differences in form, shape and size as well as the relationships and distances between critical structures.

A 3D endoscope employs two cameras for the triangulation of objects in space. A depth map could be generated, as well as a surface meshes.

A depth map is an image or image channel that contains information relating to the distance of the surfaces of scene objects from a viewpoint. A mesh is a representation of a larger geometric domain by smaller discrete cells. Surface meshes are commonly used to compute solutions of partial differential equations and render computer graphics.

A surface mesh partitions space into elements (or cells or zones) over which the equations can be solved, which then approximates the solution over the larger domain. Their vertexes define positions (usually in 3D space) along with other information such as color, normal vector and texture coordinates.

The approach of the current disclosure makes use of meshes representing a 3D object surface rather than images in the form of a 2D spatial distributions of pixels. Different methods can be used for matching the meshes. Some require the detection of common features between the meshes, and others are based on iterative methods or even ordinary differential equations (ODEs).

FIG. 7 shows a generic approach for extracting PPG signals from pixels of a 2D endoscope and building a PPG perfusion map. FIG. 7 shows a flow chart of method steps and also shows representations of the data being processed at the first four steps of the method.

Video acquisition takes place in step 70 with a standard 2D endoscope. In step 72 multiple image frames are stored.

In step 74, the motion between frames is stabilized via software. For the motion stabilization, an algorithm is used to estimate the geometric transformation between frames. Afterwards, the PPG signal is extracted in step 76 from each pixel of the stabilized video.

Finally, a PPG map (PPG amplitude and/or PPG delay) may be built in step 78 using an algorithm, such as using lock-in amplification.

FIG. 8 shows a method for processing 3D images to derive remote PPG signals in accordance with the current disclosure. FIG. 8 again shows a flow chart of method steps and also shows representations of the data being processed at the steps of the method.

The method is used to compensate the motion in endoscopic videos captured by means of 3D endoscopes, To process a PPG map.

In step 80, 3D images of a region of interest are received from a 3D endoscope. As represented in FIG. 8, each 3D image may be constituted by a pair of 2D image 82. Optionally, a depth camera may be used to obtain a depth map 84.

In step 86, a surface mesh is created of the region of interest from each of a set of the 3D images. One surface mesh is produced for each 3D image frame, i.e. for each corresponding set of 2D image frames.

A suitable surface matching approach is described in Papazov C, Burschka D. Deformable 3D shape registration based on local similarity transforms. In: Computer Graphics Forum 2011 August (Vol. 30, No. 5, pp. 1493-1502). Oxford, UK: Blackwell Publishing Ltd.

The algorithm described computes shape transitions based on local similarity transforms which allows to model not only as-rigid-as-possible deformations but also on a local and global scale. An ordinary differential equation (ODE) is formulated which describes the transition of a source shape towards a target shape. The approach assumes that both shapes are roughly pre-aligned, as frames in a motion sequence, which is a suitable assumption for this application, where meshes are collected one after the other, in a video sequence. It can thus be assumed that the deformation between consecutive frames is minimal.

Various deformable registration algorithms may be used, such as:

Feature-based methods as disclosed in Raviv D, Bronstein M M, Bronstein A M, Kimmel R. Volumetric heat kernel signatures. In: Proceedings of the ACM workshop on 3D object retrieval 2010 Oct. 25 (pp. 39-44);

Iterative algorithms (ICP algorithm) as disclosed in Ikemoto L, Gelfand N, Levoy M. A hierarchical method for aligning warped meshes. In: Fourth International Conference on 3-D Digital Imaging and Modeling, 2003. 3DIM 2003. Proceedings. 2003 Oct. 6 (pp. 434-441). IEEE;

Articulate shape registration as disclosed in Chang W, Zwicker M. Automatic registration for articulated shapes. In: Computer Graphics Forum 2008 July (Vol. 27, No. 5, pp. 1459-1468). Oxford, UK: Blackwell Publishing Ltd.

In step 88, the surface meshes are matched to each other using mesh transformations thereby providing motion compensation. In this way, the differences in perspective can be compensated. This results in a set of matched surface meshes in step 90. The transformations may be rigid or they may allow deformation. The matched surface meshes are stabilized and have a one-to-one correspondence of each vertex of a mesh (i.e. for one frame) to a corresponding vertex of the other meshes (i.e. for other frames). These vertices correspond to corresponding image voxels, and hence corresponding areas of the tissue within the region of interest.

A remote PPG signal may then be derived in step 92 from each of a set of mesh locations of the matched surface meshes, thereby to derive a set of PPG signals. In particular, a PPG signal is extracted from mesh locations in the form of each vertex of the surface mesh, or in the form of each face of the surface mesh. The PPG information is encoded now as the color of a mesh location (e.g. each vertex) whereas conventionally the PPG signal is encoded as the color of each of the pixels. From each of the vertices of the matched meshes, the PPG signals could be extracted.

Once the meshes are aligned, interpolation may be used to provide an enhanced correspondence between a location in a mesh and the same location in another mesh. Thus, it is possible for the resolution of the final achieved 3D PPG map to be the same as the pixel resolution. It is also possible to take a subgroup of the stabilized meshes and extract a PPG signal that represents the average pulsatility/perfusion of that portion of the mesh.

The set of PPG signals takes the form of a 3D PPG imaging mesh map, and it may be built using an algorithm, such as using lock-in amplification.

This method minimizes motion between the images, and provides improved perspective compensation compared to existing methods, and increases the stabilization between the frames. It enables a 3D surface map of perfusion to be generated. The use of a 3D surface map also allows for the PPG signals to be corrected to compensate for the oblique angles of the surface with respect to the camera view.

This current disclosure can be used for the stabilization of 3D endoscopic videos acquired during minimally invasive surgery. The same method can be also used for the stabilization of areas outside the body (e.g. hands, feet) using stereo cameras systems.

As mentioned above, an option is to use a depth camera in combination with a RGB camera. The depth information and therefore the 3D mesh of the imaged body part is obtained using the depth camera, and afterwards the vertex (or other mesh location) color may be assigned using the RGB camera.

Some depth cameras make use of a laser pattern for reconstructing the 3D shape of a surface being imaged (e.g. a body part). The laser projects a 2D laser pattern, which is deformed by the projection of the 2D pattern on the surface. In this way, it is possible to reconstruct the 3D shape of the surface. This type of laser grid technology is for example used already in several smartphones (e.g. iPhone 12, 13, 14) for the face unlock feature of the phone. The same hardware could be used for PPG imaging, for example integrating PPG imaging as a function of a smartphone camera.

FIG. 9 shows a processor 98 and a PPG imaging system 94 including such processor. The processor 98, and therewith the imaging system including such processor, is for processing 3D images 96 to derive remote PPG signals. The system comprises a processor 98 adapted to receive (in a passive sense under control of another device) or obtain (in an active sense under its own control and thus causing the receipt) the 3D images of a region of interest, construct a surface (e.g in the form of mesh or pointcloud) of the region of interest from each of a set of the 3D images, match the surfaces (e.g meshes or pointclouds) to each other using mesh or pointcloud transformations thereby providing motion compensation, and derive a remote PPG signal from each of a set of mesh locations or pointcloud locations of the matched surfaces (e.g the meshes or the pointclouds), thereby to derive a set of PPG signals. The set of PPG signals therewith may comprise a PPG map (e.g. delay map and or perfusion map) that pertains to a surface representing a region of interest within images.

The processor may include an input 200 for receiving the images via an input signal (that may also be represented by reference numeral 96) either or not because of a processor generated control signal causing active obtaining of the images from another device such as a camera or repository 202 storing such images. Such input 200 can comprise and/or be based on USB, Firewire, or other type for transmission of images, as known in the art. The input 200 may comprise and/or be based on wireless transmission such as Bluetooth or wifi, as known in the art. Communicative coupling may be wired and/or wireless.

The input 200 may be configured to be, or is, communicatively coupled to an image sensor 202 or image camera 202 such as a 2D- or 3D-image sensor, or a 2D-, or 3D image camera. If appropriate the image sensor may be a 3D image sensor or 3D camera. Alternatively, or additionally the input is configured to be communicatively coupled to a repository for storing images. Such repository may comprise or be memory 202 as described herein below. Images may form part of video.

The processor 98 may be or may comprise a processor circuit. It may have a central processing unit (CPU) 203 one or more memories 204 for storing data 206 used by the processor and/or instructions of computer programs 206 for implementing steps performed by the processor or another computer as defined herein. The processor or processor circuit may include busses as known in the art for communication between different parts such as between the input, output, memory and a data processor. The processor and/or processor circuit may be designed according to known contemporary electronic principles in for example silicon-based technology possibly made using semiconductor manufacturing technology. The memory may be ROM or RAM based. It may be based on electrical storage such as EPROM, FLASH DRAM, SRAM and the like and/or based on optical storage such as with CD, CD-ROM, DVD or Blue Ray or the like and/or it may be based on magnetic storage such as with magnetic hard disk or the like.

The processor or processor circuit may be part of or even take the form of a computer as comprised in a laptop or workstation, tablet or other mobile or stationary device. It may be stand alone or integrated in other devices or systems.

The processor 98 is or can be communicatively coupled to a display 100 and controls a display 100 to display the set of PPG signals 210, for example as a perfusion map and/or a delay map and/or a set of PPG waveforms. To this end the processor may have an output 208 that can be or is communicatively coupled to the display 100 and is capable of outputting the set of PPG signals 210 using an appropriate signal 210. Such output can comprise or be based on VGA, Display port, HDMI, USB or other. The output may be based on wireless transmission such as Blue tooth or wifi as known in the art.

Remote PPG sensing may be performed using a standard image sensor or camera, which receives reflected ambient light.

However, there is also the option of using hyperspectral imaging. Hyperspectral imaging (HSI) is an emerging imaging modality for medical applications that offers great potential for non-invasive disease diagnosis and surgical guidance. The objective of hyperspectral imaging is to collect a three-dimensional dataset of spatial and spectral information, known as hypercube.

As shown in FIG. 10, the hypercube is three-dimensional dataset 100 comprising two-dimensional images 102 at each of a set of wavelengths. FIG. 10 also shows a reflectance curve (i.e. the spectral signature) of a pixel in each image.

The use of hyperspectral images allows additional image processing to be performed, for example it enables a level of oxygenation of tissue to be obtained. A contact PPG probe contains two LEDs and photodetectors at two different wavelengths. By combining the readings at these two wavelengths, an estimation of the oxygen level is possible. For non-contact PPG, RGB cameras have red, green, and blue channels but they are sensitive to much broader wavelength ranges, so extracting oxygenation from a normal RGB camera is not possible. The HSI camera acquires images at specific and narrow wavelengths, so the images can be combined to extract oxygenation values.

Variations to the disclosed embodiments can be understood and effected by those skilled in the art in practicing the claimed current disclosure, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to". If the term "arrangement" is used in the claims or description, it is noted the term "arrangement" is intended to be equivalent to the term "system", and vice versa.

Any reference signs in the claims should not be construed as limiting the scope.

The invention claimed is:

1. A processor for a photoplethysmography (PPG) imaging system, for processing 3D endoscope images to derive remote PPG signals, the processor adapted to:

receive 3D endoscope images of a region of interest;

construct a surface representation of the region of interest from each of a set of the 3D endoscope images;

match the surface representations to each other using transformations thereby providing motion compensation and/or surface deformation compensation; and derive a remote PPG signal from each of a set of locations of the matched surface representations, thereby to derive a set of PPG signals.

2. The processor of claim 1, wherein the set of PPG signals comprises a PPG perfusion map based on PPG amplitude levels obtained from the endoscope images at the set of locations.

3. The processor of claim 1, wherein the set of PPG signals comprises a PPG delay map based on PPG relative delays between different locations of the set of locations.

4. The processor of claim 1, wherein the 3D endoscope images comprise stereo RGB camera images.

5. The processor of claim 1, wherein the 3D endoscope images comprise depth camera images.

6. The processor of claim 1, wherein the surface representations comprise surface meshes and the meshes comprise mesh locations comprising vertices or faces of the matched surface meshes.

7. The processor of claim 1, wherein the transformations comprise one or more of rigid transformations and transformations with deformation.

8. A system comprising:

a processor of claim 1;

one or more of: a display for displaying the set of photoplethysmography (PPG) signals to a user and a 3D camera for capturing the 3D endoscope images of the region of interest.

9. The system of claim 8, comprising an endoscope and the 3D camera, wherein the 3D camera is mounted at a distal end of the endoscope.

10. A computer-implemented method for processing 3D endoscope images to derive remote photoplethysmography (PPG) signals, comprising:

receiving 3D endoscope images of a region of interest;

constructing a surface representation of the region of interest from each of a set of the 3D endoscope images;

matching the surface representations to each other using transformations thereby providing motion compensation and/or surface deformation compensation; and deriving a remote PPG signal from each of a set of surface representation locations of the matched surface representations, thereby to derive a set of PPG signals.

11. The method of claim 10, comprising providing the set of PPG signals as a PPG perfusion map based on PPG amplitude levels obtained from the images at the surface representation locations.

12. The method of claim 10, further comprising providing the set of PPG signals as a PPG delay map based on PPG relative delays between different locations of the surface representation.

13. The method of claim 10, wherein the transformations comprise one or more of rigid transformations and transformations with deformation.

14. The method of claim 10, wherein the surface representations comprise surface meshes and the locations are mesh locations comprising vertices or faces of the matched surface meshes.

15. A non-transitory computer-readable storage medium having stored a computer program comprising instructions to perform a method comprising:

receiving 3D endoscope images of a region of interest;

constructing a surface representation of the region of interest from each of a set of the 3D endoscope images;

matching the surface representations to each other using transformations thereby providing motion compensation and/or surface deformation compensation; and deriving a remote photoplethysmography (PPG) signal from each of a set of surface representation locations of the matched surface representations, thereby to derive a set of PPG signals.

16. A processor configured to:

receive 3D endoscope images of a region of interest;

construct a surface representation of the region of interest from each of a set of the 3D endoscope images;

match the surface representations to each other using transformations thereby providing motion compensation and/or surface deformation compensation; and derive a remote photoplethysmography (PPG) signal from each of a set of locations of the matched surface representations, thereby to derive a set of PPG signals.

\* \* \* \* \*